United States Patent [19]

Averill

[11] 4,217,666
[45] Aug. 19, 1980

[54] TIBIAL PROSTHESIS HAVING A U-SHAPED INTRAMEDULLARY STEM

[75] Inventor: Robert G. Averill, Ringwood, N.J.

[73] Assignee: Minnesota Mining and Manufacturing Company, Saint Paul, Minn.

[21] Appl. No.: 27,518

[22] Filed: Apr. 5, 1979

[51] Int. Cl.² ............................................. A61F 1/24
[52] U.S. Cl. ................................... 3/1.911; 128/92 C
[58] Field of Search .............................. 3/1.91, 1.911; 128/92 C

[56] References Cited

U.S. PATENT DOCUMENTS

| | | | |
|---|---|---|---|
| 3,893,196 | 7/1975 | Hochman | 3/1.91 |
| 4,081,866 | 4/1978 | Upshaw et al. | 3/1.911 |

FOREIGN PATENT DOCUMENTS 2122390  1/1973  Fed. Rep. of Germany ............ 3/1.911

Primary Examiner—Clifford D. Crowder
Attorney, Agent, or Firm—Cruzan Alexander; Donald M. Sell; Edward T. Okubo

[57] ABSTRACT

A tibial prosthesis which interacts with a femoral prosthesis to provide a knee joint replacement is disclosed. The prosthesis comprises a tibial plateau platform provided with an intramedullary stem having a generally U-shaped cross section allowing for retention of the cruciate ligaments of the knee joint while still achieving adequate anchorage of the device to the proximal end of the tibia.

10 Claims, 6 Drawing Figures

TIBIAL PROSTHESIS HAVING A U-SHAPED INTRAMEDULLARY STEM

BACKGROUND OF THE INVENTION

The present invention relates to a tibial prosthesis which interacts with a femoral prosthesis to provide a knee joint replacement. The prosthesis is intended to be implanted in the proximal end of the tibia. The prosthesis of the present invention utilizes an intramedullary stem having a generally U-shaped cross section. The U-shaped cross section stem allows for retention of the cruciate ligaments of the knee while also increasing stability of the tibial prosthesis component.

The natural knee joint comprises the bottom (distal) end of the femur and the upper (proximal) end of the tibia. Bearing action occurs between two condyles on the lower surface of the femur and the complementary upper surface plateaus of the tibia, separated by intermediary cartilage pads, the meniscii. Connection of the tibia to the femur is provided by means of ligaments, including the cruciate ligaments of the knee, which are strong thick bundles situated between the condyles.

Movement of the normal knee is complex, including rolling, gliding and axial rotational motions. Not only do the cruciate ligaments provide connection between the femur and the tibia, assure joint stability and help to absorb stresses applied to the knee but they are also largely responsible for providing the proper combination of rolling and gliding motions and transitions between such motions which characterize the normal knee action.

Hip joint prosthetic devices are becoming relatively common and have had a fairly good record of success. Knee joint implants are of more recent design, have generally been less successful than hip implants and their long term stability has not yet been proven. The knee joint is subject to greater stresses than any other joint in the body. It must support the entire weight of the body above the knee and must do so throughout the various relative angular relationships of femur and tibia. Ideally, a knee joint prosthesis should provide the same action as the natural human knee—a complex combination of rotational, rolling and sliding/gliding movements.

Until recently, endoprosthetic knee joint devices comprised separate femoral and tibial components linked together with a coupling pin in the form of a mechanical hinge, having a single axis of rotation, fixed to the femur and the tibia, respectively, each component having a long intramedullary stem for bone fixation. These so-called hinge-type devices were not always duplicative of knee joint biological hingings since they had a single axis of rotation while the human knee joint which these devices sought to emulate involves polycentric movements. Thus, many variations of hinges, spindles, ball and socket and double hinges were used in an attempt to duplicate the complex natural knee motions; however, none of the simplified approximations could accurately do so. A common feature of these so-called hinged implants was that they provided positive mechanical connection between the femoral and tibial components so that the natural connective ligaments did not need to be and, in fact, could not be retained. Also, because of the bulk of these devices, it was necessary to remove a considerable amount of natural bone to allow space for the device, such removal reducing bone reserve which might be needed for future corrective measures.

A further disadvantage of the hinge-type devices was their limited axial rotation causing direct transmission of end limit forces through the structure thereby tending to loosen fixation of the femoral and tibial components. For this reason, practically all of these devices used all-metal, deep-bone penetrating intramedullary stems for purposes of fixation.

Examples of these hinge-type knee prosthetic devices can be found in Lagrange U.S. Pat. No. 3,688,316; Bousquet U.S. Pat. No. 3,696,446; Goldberg U.S. Pat. No. 3,765,033; Findlay U.S. Pat. No. 3,886,601; Lagrange U.S. Pat. No. 3,918,101 and Arkangel U.S. Pat. No. 4,001,896.

The newer implantable knee devices generally mechanically uncouple the femoral and tibial components; instead of connecting the components by a pivot pin or other mechanical linkage they are held in mutual bearing engagement by the biological structure of the knee, that is, by indirect coupling through the muscular, capsular and ligamentous components of the natural joint. These devices usually comprise a combination of a femoral device constructed of metal with spaced runners to replace the natural condyles, and a plastic tibial device to replace the natural plateau, the devices having usually convex and concave mating surfaces, respectively.

SUMMARY OF THE INVENTION

The present invention relates to these newer type knee devices of the non-hinged type and further relates only to the tibial component thereof. The device of the present invention can be used in combination with a large number of femoral components. Some exemplary femoral devices are disclosed in Link U.S. Pat. No. 3,715,763; Averill U.S. Pat. No. 3,728,742; Helfet U.S. Pat. No. 3,748,662; Marmor U.S. Pat. No. 3,852,830 and Lee U.S. Pat. No. 3,958,278.

The tibial prosthesis of the present invention comprises a tibial plateau platform provided with an intramedullary stem having a generally U-shaped cross section thereby allowing for retention of the cruciate ligaments of the knee joint while still achieving adequate anchorage of the device to the proximal end of the tibia.

BRIEF DESCRIPTION OF THE DRAWINGS

The invention will be better understood by reference to the following description of an exemplary embodiment taken in conjunction with the accompanying drawings, in which.

DETAILED DESCRIPTION OF THE INVENTION

Figure 1:
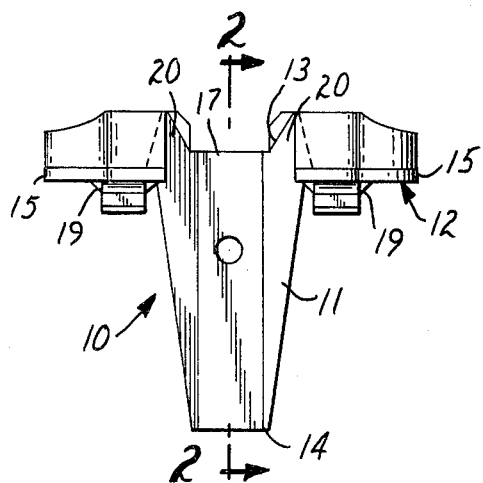
FIG. 1 is an elevational view of the tibial prosthesis of the present invention.

The present invention relates to the tibial component of a non-hinged knee prosthesis. A problem encountered in the designing of these devices has been the apparent need to compromise between the provision of firm and lasting mechanical attachment of the components to the leg bones on the one hand and the need for retention of the natural ligaments on the other. Of particular concern are the cruciate ligaments which are probably the most important ligaments of the knee joints. Unfortunately, these cruciate ligaments work through the center of the knee so that retention of these important ligaments precludes the usage of the intramedullary stem attachment which was provided on the majority of hinged-type knee replacements since these stems or spikes would also need to be located at the center of the components. In other words, it appeared impossible to have both an opening for the cruciate ligaments in the center of the implantable components and intramedullary fixation stems in the center of the components.

The problem was met in the case of the femoral component since, because of its wrap-around design, it could make good geometric and area contact with the end of the femur. In addition, the knobbed end of the femur is quite large and thus provides sufficient bone around the cruciate ligaments so that several smaller stems can be securely placed within solid bone. Further, the femoral component is usually made of metal and hence is not particularly subject to wear or breakage.

The tibial component presented more of a problem. Being quite small and being normally made of plastic, it does not have the mechanical stability and strength of the metal femoral component. Examination of the prior art shows that various protrusions, short pegs and keying designs were provided, mainly in an effort to increase the contact surface area so that the bone cement used to adhere the component to the tibia would be more effective. However, it is well known in the art that bone cement does not guarantee firm and lasting adhesion to bone. Further, these devices are frequently employed in treatment of arthritic conditions where bone quality is generally poor and usually subject to even further degeneration. The means for attachment of these prior art tibial devices is so shallow as to provide a poor moment arm to resist displacement torque yet these devices are used in a joint which is subject to substantial tensional loadings.

Essentially, the surgeon understood that a problem existed. However, if the cruciate ligaments were sound, it was felt to be prudent to retain the ligaments and use a potentially unstable tibial component with full knowledge that a high proportion of operating stresses would have to be carried by the ligaments. Then, if the device loosened at a later date, the cruciate ligaments could be removed at that time and a more stable hinged knee prosthesis having an intramedullary stem substituted.

The present invention provides a tibial component 10 which substantially resolves the problem and eliminates the need for compromise. The tibial component of the present invention provides for both cruciate ligament retention and intramedullary stem attachment. Referring more particularly to the drawings, it will be seen that the tibial component 10 is provided with an intramedullary stem or spike 11 which has a generally tapered U-shaped cross section so that such spike 11 can be attached to the tibial plateau platform 12 around the periphery of a central opening 13 which allows for passage of the important cruciate ligaments. The attachment area is U-shaped so that the central opening 13 remains fully open posterially to allow for passage of and not to impede the action of the cruciate ligaments.

It is preferred that the spike 11 be of constant "radius" as it diminishes in width toward a tapered point 14 so that the spike 11 can be easily driven or forced into the intramedullary cavity of the resected tibia. Similarly, the cross section can diminish in thickness toward the point 14 because the need for strength and stiffness diminishes with distance from the plateau platform 12. Thus, spike 11 will be inclined upwardly and outwardly from the point 14 to its area of attachment to tibial plateau platform 12. It is preferred that the penetration tip of the spike 11 be flattened or slightly rounded rather than sharp and pointed. While it is preferred that the intramedullary stem have a generally U-shaped cross section, it should be understood that variations such as a crescent shaped channel are also contemplated. It is, however, preferred to use a cross sectional form which is other than a straight flat shape as such would be more subject to bending and hence be less stiff although portions of the spike, particularly near the point, could be flat.

Since plastic does not generally possess the mechanical stability, stiffness and strength of metal, it is preferred to make the spike 11 of metal, preferably of medical grade cobalt-chromium alloy. Alternatively, stainless steel or titanium may be used. For similar reasons, the plateau platform 12 or at least the underlying portion of the platform which is directly attached to the spike 11 should also be made of similar metal. The bearing surface 26 of the tibial device 10 which must react against the condylar surfaces of a mating femoral device (not shown) should preferably be made of a durable, low-friction, physiologically acceptable plastic, as for example, Ultra High Molecular Weight Polyethylene. The plastic bearing inserts 25 should be firmly attached to the metal plateau platform 12 and be suitably restrained from movement.

Figure 3:
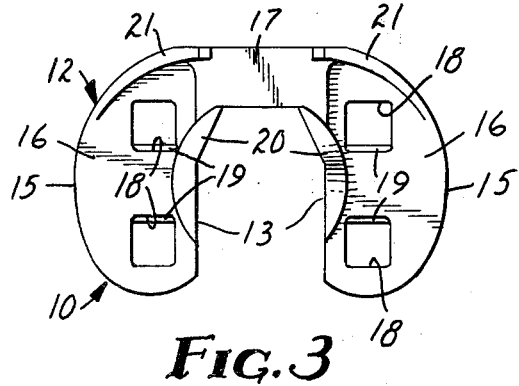
FIG. 3 is a top plan view of the tibial plateau platform of the tibial prosthesis of FIG. 1.
Figure 4:
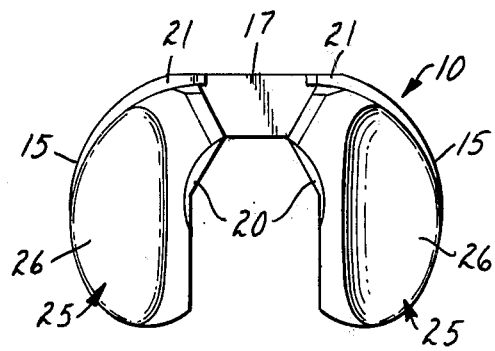
FIG. 4 is a top view of the tibial prosthesis of the present invention showing the bearing inserts which interact with the condylar surfaces of a femoral prosthesis in place.
Figure 5:
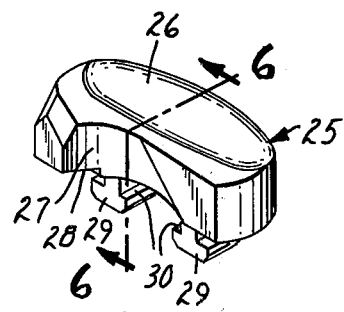
FIG. 5 is a perspective view of a bearing insert of FIG. 4.
Figure 6:
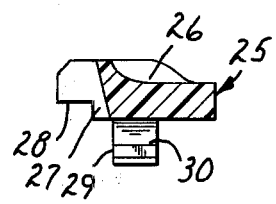
FIG. 6 is a sectional view of the bearing insert taken along the line 6—6 of FIG. 5.

The plateau platform 12 is generally U-shaped as will clearly be seen in FIG. 3. As presently preferred, each leg portion 15 is recessed at its juncture with the thicker body portion 17 of the U to provide a flat, generally D-shaped platform 16 for bearing insert 25. A pair of spaced apertures 18 is provided in each platform 16. Although the apertures 18 are shown as being square, other shapes are contemplated provided that the aperture has at least one straight edge for a purpose to be described hereafter. Each aperture 18 is formed with a depending ear 19 along one edge thereof. Each platform 16 is formed with an upwardly extending retainer wall member 20 along the interior of each leg portion 15. The portion of the wall member 20 adjacent platform 16 is smoothly upwardly arcuate (convex) while the opposite side follows the contour of the spike 11 and thus is angularly contoured. (See FIG. 3). An arcuately contoured upwardly extending retaining ridge 21 is provided along the edge of each platform 16 at the juncture of the leg portion 15 with the body portion 17 of the U. It will be appreciated that numerous other means for removably attaching the bearing inserts 25 to plateau platform 12 are possible and such alternatives are considered to be within the scope of the present invention.

It is preferred that the surfaces of the spike 11 be texturized in some fashion as with grooves, perforations, ridges or the like to increase the interaction of same with the bone of the tibia or with intervening bone cement. Even more preferred would be the provision of porous surfaces so as to permit for bone ingrowth, as is known in the art. It is also preferred that portions of the underside of the tibial plateau platform 12 be provided with similar surface texture or porosity.

Figure 2:
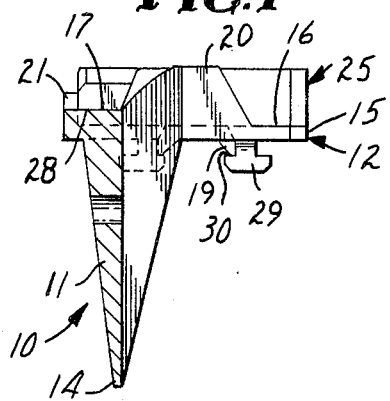
FIG. 2 is a sectional view taken along the line 2—2 of FIG. 1.

Bearing insert 25 is generally kidney shaped and is sized to fit onto platform 16 and within the confines of retainer wall member 20 and retaining ridge 21. The outer portion of the upper surface of bearing insert 25 is scooped out to form a smoothly arcuately concave bearing surface 26 for the mating condylar surface of a femoral prosthesis (not shown). The inner edge of bearing insert 25 is provided with an arcuate recess 27 shaped complementarily to the smoothly upwardly arcuate contour of the wall member 20. The bottom surface of bearing insert 25 is substantially flat. In order to allow bearing insert 25 to fit onto platform 16, the portion of the bottom surface of said insert extending beyond the recess formed in the leg portion 15 of platform 16 is removed to a depth correspondng to the depth of said recess. The thus undercut portion forms ledge 28 which fits and lies upon body portion 17 of the U when bearing insert 25 is positioned onto platform 16. Projecting from the bottom surface of insert 25 and positioned in alignment with the spaced apertures 18 in platform 16 are a pair of spaced pegs 29. The free end of each peg 29 is larger than the peg itself such that a ridge 30 is provided along at least one edge of the peg. In the illustrated embodiment, ridge 30 is provided along two opposite edges although only the interior ridge 30 is required. As clearly shown in FIG. 2, ridges 30 engage the depending ears 19 of the corresponding apertures 18, thus securely attaching insert 25 to platform 12.

In order to facilitate insertion of pegs 29 into apertures 18, the leading edges of the enlarged ends of peg 29 are chamfered as shown in the drawings.

The tibial prosthesis of the present invention, in combination with a femoral prosthesis having a medial slot for passage of the cruciate ligaments, provides a prosthetic device affording substantial congruence between the femoral condyles and the tibial plateau thus providing the rotational, sliding, rolling and gliding action of a functional knee.

What is claimed is:

1. A tibial prosthesis for interaction with a femoral prosthesis having a central slot therein for passage of the cruciate ligaments, said tibial prosthesis comprising a generally U-shaped tibial plateau platform, a bearing insert removably attached to each leg of said U-shaped platform for sliding contact with the condylar surface of said femoral prosthesis, an intramedullary fixation stem attached to said platform along one edge thereof, said stem having a generally tapered U-shaped cross section, the attachment area of said stem to said platform being U-shaped to thereby define a central opening to allow for passage of and permit unimpeded action of the cruciate ligaments.

2. A tibial prosthesis according to claim 1 wherein said platform is fabricated from a metal or metal alloy.

3. A tibial prosthesis according to claim 2 wherein the bottom surface of said platform is texturized.

4. A tibial prosthesis according to claim 1 wherein said bearing insert is fabricated from a physiologically acceptable plastic material.

5. A tibial prosthesis according to claim 1 wherein said intramedullary fixation stem has a constant "radius" as it diminishes in depth from the attachment area to a tapered point at its free end.

6. A tibial prosthesis according to claim 5 wherein said intramedullary fixation stem has a cross section which diminishes in thickness from said attachment area to said point.

7. A tibial prosthesis according to claim 6 wherein the end of said point is flattened or rounded.

8. A tibial prosthesis according to claim 7 wherein said intramedullary fixation stem is fabricated from a metal or metal alloy.

9. A tibial prosthesis according to claim 8 wherein the surfaces of said intramedullary fixation stem are texturized.

10. A tibial prosthesis according to claim 1 wherein the cross section of said intramedullary fixation stem is lunate, has a constant radius as it diminishes in depth and thickness from the attachment area to a tapered point having a rounded end, is fabricated from a metal or metal alloy and the surface thereof are texturized.

* * * * *